United States Patent
Brandsey et al.

[19]

[11] Patent Number: 6,051,005
[45] Date of Patent: *Apr. 18, 2000

[54] LAPAROSCOPIC KNIFE

[76] Inventors: Edward P. Brandsey, 1207 Portage La., Woodstock, Ill. 60098; Mrugendra Gandhi, 335 Fox Run, Green Oaks, Ill. 60048

[ * ] Notice: This patent issued on a continued prosecution application filed under 37 CFR 1.53(d), and is subject to the twenty year patent term provisions of 35 U.S.C. 154(a)(2).

[21] Appl. No.: 09/161,050

[22] Filed: Sep. 25, 1998

Related U.S. Application Data

[60] Provisional application No. 60/060,122, Sep. 26, 1997.

[51] Int. Cl.⁷ .................................................... A61B 17/00

[52] U.S. Cl. ................................................................ 606/148

[58] Field of Search ...................................... 606/139, 144, 606/145, 151, 157, 147, 148

[56] References Cited

U.S. PATENT DOCUMENTS

| | | | |
|---|---|---|---|
| 5,281,237 | 1/1994 | Gimpelson | 606/144 |
| 5,376,096 | 12/1994 | Foster | 606/147 |
| 5,387,221 | 2/1995 | Bisgaard | 606/148 |
| 5,540,704 | 7/1996 | Gordon et al. | 606/144 |
| 5,817,112 | 10/1998 | Christoudias | 606/148 |

*Primary Examiner*—Michael Buiz
*Assistant Examiner*—Vikki Trinh
*Attorney, Agent, or Firm*—Dick and Harris

[57] ABSTRACT

A surgical instrument is provided for use during laparoscopic surgical procedures, such as gall bladder removal operations. The instrument includes an elongated shaft, with a short, wedge-shaped blade extending at an angle to the longitudinal axis of the shaft. A handle is positioned at the opposite end of the shaft, from the blade. The blade is configured to be inserted into and through a surgical sheath, to be able to perform incisions in a patient's abdomen, by upward pulling motions on the instrument, while the handle remains outside the patient.

14 Claims, 3 Drawing Sheets

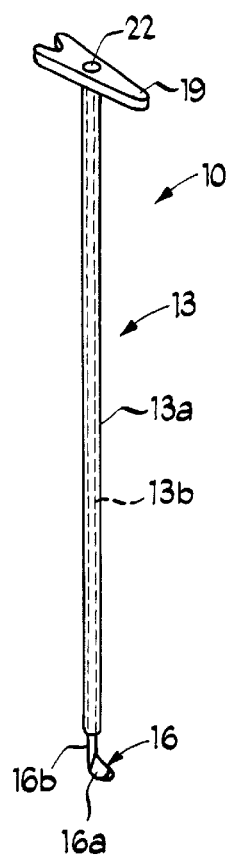
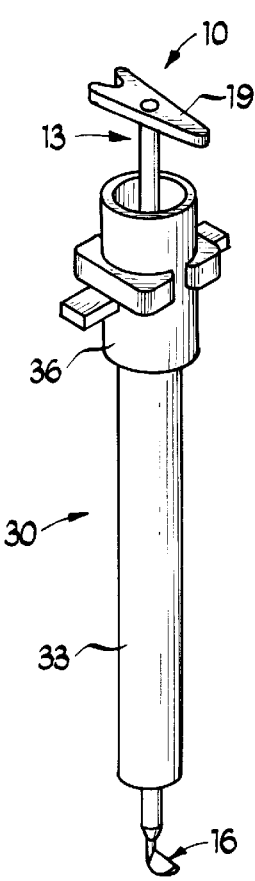
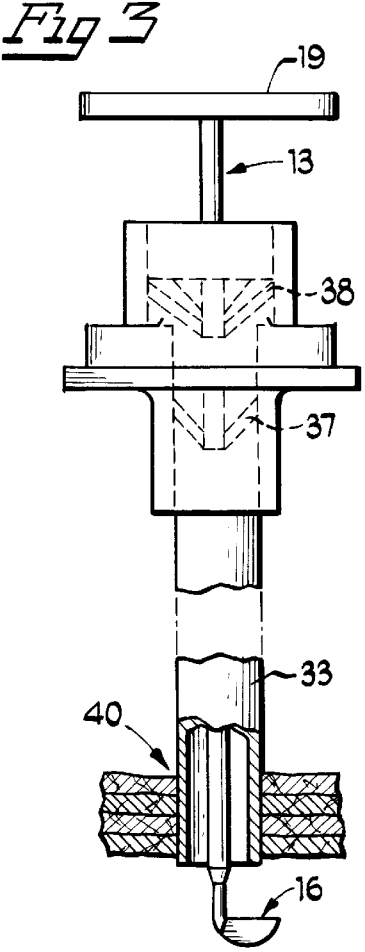
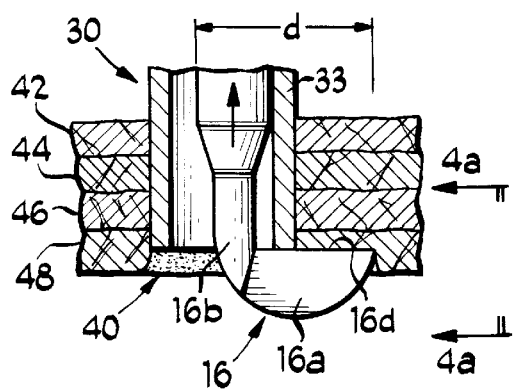
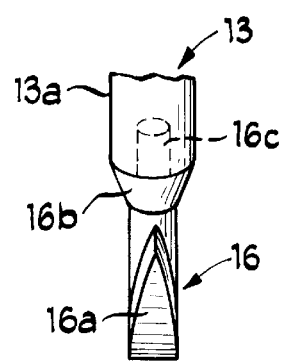

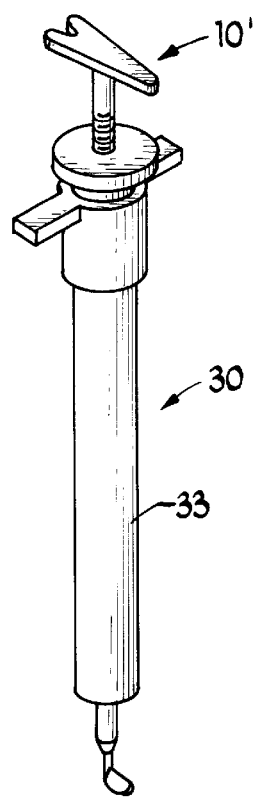
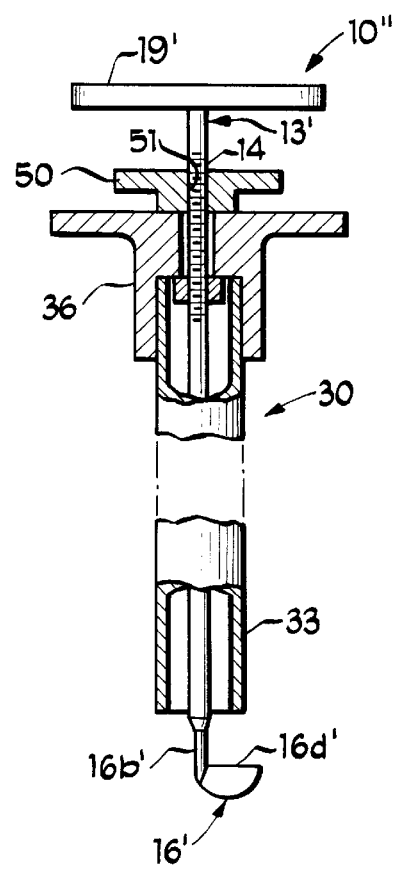
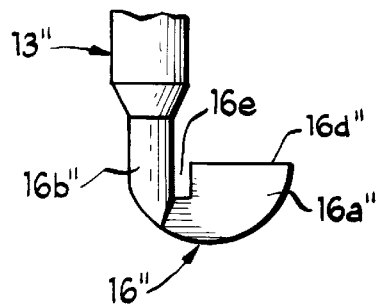
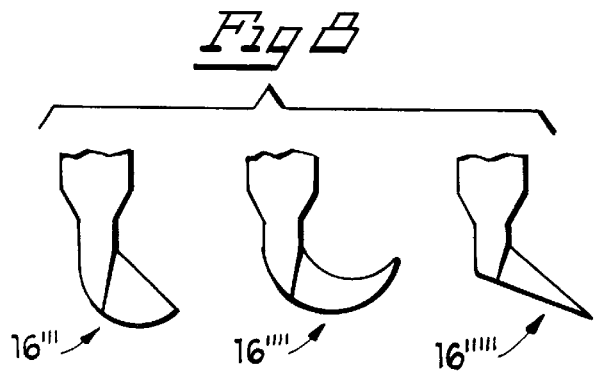
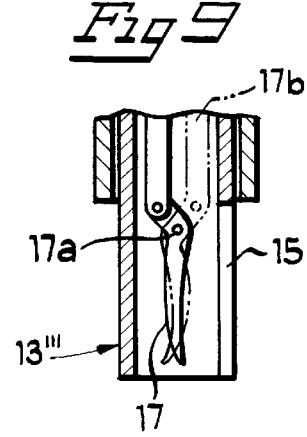

LAPAROSCOPIC KNIFE

This application claims priority under 35 U.S.C. §119(e) of U.S. provisional patent application Ser. No. 60/060,122, filed Sep. 26, 1997.

BACKGROUND OF THE INVENTION

1. Field of the Invention

The present invention relates to surgical instruments for the performance of procedures such as laparoscopic surgical procedures, for example, gall bladder removal operations.

2. The Prior Art

During a typical laparoscopic surgical procedure, such as the removal of a gall bladder, four incisions are made in the patient's abdomen at spread apart locations. The incision descends through the abdominal wall comprising the skin, subcutaneous fat layer, the abdominal muscle layer, the fascia, and the peritoneum.

Through one of the incisions, a laparoscopic sheath will be inserted. A typical laparoscopic sheath comprises a tube, made of plastic or metal, which has a valve structure at one end. The purpose of the sheath is to permit the injection of carbon dioxide gas through the sheath and into the abdominal cavity in order to inflate the abdominal walls to provide room in which to perform the laparoscopic surgical procedure. A number of valve flaps are positioned around the inner periphery of the tube. These valve flaps, which extend in radially inwardly from the inner periphery of an upper section of the sheath, also extend downwardly toward the abdominal cavity and overlap one another, to permit the insertion of surgical instruments down through the tube while maintaining a substantial seal around the instrument to minimize leakage of the carbon dioxide gas and maintain the inflation of the abdominal wall.

During a typical gall bladder surgical procedure, a miniaturized (typically flexible) camera tube, e.g. a laparoscopy (e.g. fiber optic) camera is inserted. Other surgical instruments may be inserted through the other incisions. After the organ has been tied off and then severed, the organ is removed through one of the incisions, typically through the incision through which the laparoscopic sheath has been inserted. Typically, the sheath will be removed and a grasping instrument inserted through the incision in order to grasp the severed and tied off organ and pull it through the relatively small, e.g. 10 mm, incision.

However, often the organ may be enlarged beyond normal size and/or may be filled with stones. While the stones in a stone-filled gall bladder can occasionally be reduced by manual crushing prior to removal of the gall bladder, in the cases when such stones cannot be crushed or in the case of an otherwise abnormally large gall bladder or other organ, the incision through which the organ is to be removed must be enlarged to enable removal of the organ. The outermost skin incision is easily lengthened through the use of a scissors or scalpel. However, to lengthen the incision through the abdominal muscles and the final layers of fascia and peritoneum in the abdominal cavity, small surgical scissors must be inserted through the aperture and the incision must be lengthened at those layers in a blind manner.

Such additional procedures, while typically not involving any additional danger to the patient, do involve added time to the length of the surgical procedure and as well increase the size of the incisions, thus increasing the number of stitches or other surgical repair techniques which must be employed, and increasing the area which must undergo healing.

It would be desirable to provide a more effective and more easily accomplished method in which to enlarge such incisions in a manner which will permit such enlargements to be made more quickly and in a more precise and controlled manner.

These and other objects of the invention will become apparent in light of the present specification and drawings and claims.

SUMMARY OF THE INVENTION

The present invention is directed to a laparoscopic knife apparatus for use in laparoscopic procedures, such as the removal of a gall bladder. The invention comprises a knife apparatus which is intended to be used with a laparoscopic sheath to form an enlargement of an abdominal laparoscopic incision from inside the abdomen.

The laparoscopic knife comprises a shaft having sufficient length to be passed through a laparoscopic sheath and into the abdominal cavity of a patient while retaining sufficient length outside of the laparoscopic sheath in order to enable manipulation of the laparoscopic knife by the surgeon. At one end of the shaft is situated a blade which is appropriately sized to enable passage through the tube of the laparoscopic sheath. At the opposite end of the sheath is a handle for manipulation of the laparoscopic knife.

Preferably, the blade is oriented on the shaft in such a manner that the cutting edge faces upwardly, toward the handle of the knife. The blade edge may be straight or it may be concavely curved upward. The edge of the blade may be at generally right angles to the shaft or it may be at an obtuse angle relative to the shaft in order to give the blade additional length. A notch may be provided in the blade adjacent the juncture of the blade to the shaft. This notch may be provided to enable the knife to engage the lower end of the sheath tube, so that the sheath and the blade may be connected to form a composite tool to enable the sheath to be used as an additional stabilizing handle during performance of the incision.

Preferably, the handle is configured as an elongated member, generally perpendicular to the shaft and oriented such that the longitudinal axis of the handle is parallel to the longitudinal axis of the blade, so that by observing the orientation of the handle, the operator is informed as to the direction in which the blade is pointed. Indicia may be provided on the top of the handle to further indicate the direction in which the blade is pointed.

In an alternative embodiment of the invention, a locking mechanism may be provided on the shaft of the knife to enable the knife to be locked into a joint configuration with the sheath to further enable the sheath to function as an augmented handle for the laparoscopic knife.

In a further alternative embodiment of the invention, the blade may be articulably connected to the shaft between a retracted and extended position. In this manner, an enlarged knife blade may be mounted within the shaft and stowed in a retracted position while the shaft of the knife is being passed through the surgical sheath tube. Upon suitable positioning of the blade end of the shaft in the patient's abdomen, a suitable mechanism may be actuated, causing the knife blade to pivot outwardly relative to the knife shaft to project laterally into the desired cutting position. A locking mechanism may be provided in order to fix the knife blade in the deployed position during performance of the incision procedure. After performance of the incision procedure, the locking mechanism may be released, permitting the blade to be retracted so that the knife and/or the surgical sheath can be removed without excessive manipulation required relative to the incision and/or the creation of additional, undesired incisions in the patient's abdomen wall.

BRIEF DESCRIPTION OF THE DRAWINGS

FIG. 1 is a perspective view of the laparoscopic knife according to one preferred embodiment of the invention.

FIG. 2. is a perspective view of the laparoscopic knife as inserted through a laparoscopic surgical sheath.

FIG. 3 is a side elevation, partially in section, showing a surgical sheath inserted through the abdomen wall of a patient, with the laparoscopic knife of the embodiment of FIG. 1 inserted therethrough.

FIG. 4 is a side elevation in section, showing the blade end of a laparoscopic knife according to the present invention being used to perform an incision into the abdominal wall of a patient.

FIG. 4a is a side elevation of the knife blade, taken along line 4a—4a of FIG. 4.

FIG. 5 is a perspective view showing a laparoscopic knife according to an alternative preferred embodiment of the invention, inserted into a surgical sheath.

FIG. 6 is a side elevation, partially in section, of the laparoscopic knife of the alternative embodiment of FIG. 5.

FIG. 7 is a fragmentary enlarged view of the blade end of a laparoscopic knife according to another alternative embodiment of the present invention.

FIG. 8 illustrates further alternative configurations for the blade end of the laparoscopic knife of the present invention.

FIG. 9 is a side elevation, partially in section, showing an end of articulable laparoscopic knife, according to still another alternative embodiments of the invention.

BEST MODE FOR CARRYING OUT THE INVENTION

Figure 10:
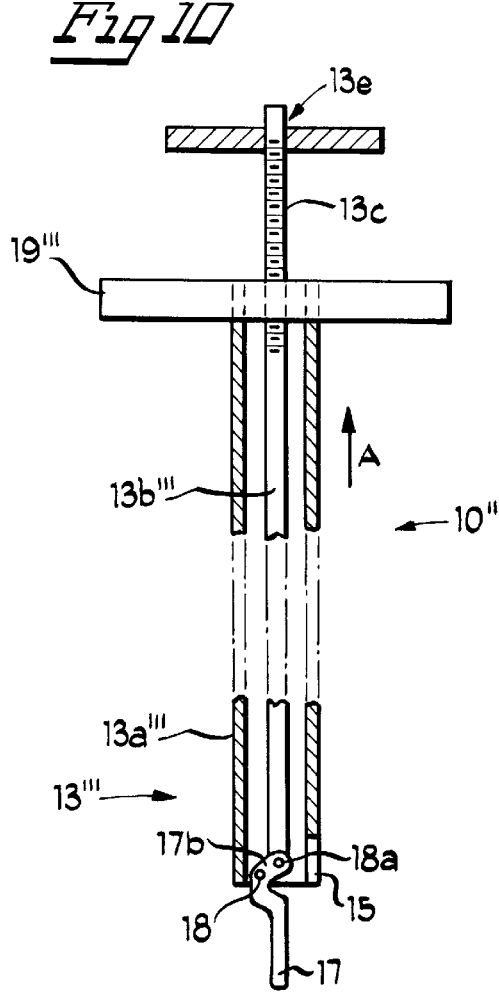
FIG. 10 is a side elevation, partially in section, illustrating, in particular, the articulating mechanism for the articulating laparoscopic knife of the embodiment of FIG. 9.

While this invention is susceptible of embodiment in many different forms, there is shown in the drawings, and will be described in detail herein, several specific embodiments, with the understanding that the present disclosure is to be considered as an exemplification of the principles of the invention and is not intended to limit the invention to the embodiments illustrated.

In the drawings several embodiments are illustrated, in which elements are similar in function or configuration are provided with like reference numerals augmented by primes (') or multiple primes.

FIG. 1 is a perspective view of laparoscopic knife 10, including shaft 13, blade 16 and handle 19. According to one embodiment of the invention, shaft 13 is formed from a tube 13a, which may be configured from a stainless steel material, such as a 300 series stainless steel, as identified by those knowledgeable in the art of manufacturing surgical instruments. A center shaft 13b may be insertably received inside of tube 13a. Shaft 13b may be fabricated from a nickel silver wire in order to give shaft 13a additional stiffness. Handle 19 is likewise preferably fabricated from a stainless steel silver material. An aperture 22 may be tapped to receive the end of tube 13a, which preferably will be threaded at its handle end to meet with internal threads on the inside of aperture 22. Nickel silver shaft 13b preferably is soldered, such as silver soldered into tube 13a. Once the end of tube 13a has been threadably engaged into handle 19, both tube 13a and nickel silver wire 13b may be soldered permanently into place.

Blade 16 is preferably fabricated from a hard, durable edge holding stainless steel material, such as the material known as ATS-34 stainless steel. Preferably, by heat treatment, the blade, which may be ground using known knife making techniques, is thereafter heat treated to a hardness on the Rockwell Scale of 60. According to one embodiment of the invention, blade 16 has a cutting portion 16a which is generally semicircular in shape. A small shaft 16b is provided to attach blade 16 to shaft 13. Preferably, shaft 16b is insertably received into the end of tube 13a and soldered (e.g. silver soldered) into place. The end 16c of shaft 16b is shown insertably received inside tube 13a of shaft 13 in FIG. 4a. The bottom rounded portion of blade portion 16a is blunt and, in a preferred embodiment of the invention, approximately 2.5 mm in thickness from side to side. Edge 16d, having a hardness of Rockwell 60, is extremely sharp and durable and can only cut with an upward pull along the direction of shaft 13. Preferably, the distance d (see FIG. 6) from the back of shaft 13 to the point of blade 16, will be slightly less than 10 mm. This will permit easy passage of the blade end of knife 10 through the tube of substantially all conventionally known laparoscopic sheaths, which typically have interior diameters of approximately 10 mm. The length of cutting edge 16d preferably will be approximately 5 mm. Since shaft 13 will have an outside diameter of approximately 4 mm, once positioned in place, shaft 13 can be skewed slightly with respect of the axis of the tube of the laparoscopic sheath so that substantially all of the 5 mm of edge will project outwardly relative to the side wall of the laparoscopic tube.

In order to enable the surgeon to know which direction blade 16 is pointing, preferably handle 19 is elongated and may be pointed at one end (e.g. or in the shape of an arrowhead, as illustrated) with the longitudinal axis of the handle 19 parallel to and pointing in the same direction as blade edge 16d. In this way, direct observation of blade 16, for example by use of a laparoscopic television camera, is not necessary in order to know which direction the blade is pointing, although the cutting procedure will typically be observed using the inserted camera, as previously described. Alternatively, handle 19 may have some other suitable shape such as oval, round, etc., but may be provided with indicia, such as an arrow etched into its upper surface, for purposes of indicating the direction in which blade 16 is pointing.

FIG. 2 illustrates laparoscopic knife 10 insertably received within a surgical sheath 30, such as are commonly known in laparoscopic surgical procedures. Surgical sheath 30 includes tube 33, which, as previously discussed, may have a typical nominal interior diameter of 10 mm. Atop tube 33 is valve section 36 which may be provided in a conventional manner with a suitable switchable gas valve for receiving gas for inflating the abdominal cavity of the patient. For simplicity of illustration, the gas valve elements, which are known in the art, have been omitted. In addition, as illustrated in FIG. 3, a plurality of valve flaps 37 and 38 are provided on the interior of valve section 36 of sheath 30. Valve flaps 37 and 38 typically are formed as generally rectangular sheets of elastomeric material and extend radially inwardly from the interior surface of the passage toward the center of the passage in an overlapping manner. In addition, valve flaps 37 and 38 typically point "downward" toward the insertion end of tube 33. Valve flaps 37, 38 will permit an object to be pushed through sheath 30 and down tube 33 into the abdominal cavity of the patient, once sheath 30 has been itself been inserted through the incision 40 (see FIG. 3) in the patient's abdominal wall.

The cutting procedure involving use of the laparoscopic knife 10 typically will proceed as follows. Referring to FIG. 4, the tube 33 of a laparoscopic sheath 30 will already been inserted into an incision 40 in a patient's abdominal wall. The abdominal wall typically will comprise skin 42, a subcutaneous fat layer 44, the fascia 46 and the peritoneum 48. If it is determined, upon severing and tying off of the organ to be removed, that the organ will not adequately and safely pass through incision 40, then whatever surgical instruments are currently present within tube 33 are removed. Laparoscopic knife 10 is then inserted into tube 33. The open end of tube 33 at this point will be somewhat below the level of peritoneum 48 and thus projecting into the abdominal cavity. Laparoscopic knife 10 will be angled slightly so that blade edge 16d is brought to bear against the mouth of tube 33. Sheath 30 and knife 10 are then pulled upwardly simultaneously, preferably while being observed through a laparoscopy camera on a TV screen in the operating theater.

As previously mentioned, preferably knife 10 is held at a slight angle relative to the longitudinal axis of tube 33 so that substantially all of blade portion 16a of blade 16 extend outwardly beyond the side wall of tube 33. Thus, an upward cut of approximately 5 mm in horizontal length may be achieved at each opposite end of the peritoneal incision (i.e., on opposite sides of tube 33. In this manner, the length of the incision in the peritoneum, which typically is initially 10 mm in length, can be effectively substantially doubled from within, without needing to attempt an enlargement of the incision from the outside utilizing small scissors. The peritoneal incision is thus accomplished much more quickly, much more easily and much more precisely using the laparoscopic knife of the present invention when compared to prior techniques for enlarging a laparoscopic incision.

FIGS. 5 and 6 illustrate an alternative embodiment of the present invention. As described with respect to the embodiment of FIGS. 1–4a, the tube of the laparoscopic sheath is utilized to provide a locating mechanism for the laparoscopic knife. During the performance of the actual incision making, the laparoscopic sheath necessarily is pulled upward relative to the patient's abdominal wall in order to form the incision. At the same time, however, in order to maintain the laparoscopic sheath 30 in a steady and controlled orientation, the surgeon must actually press downward slightly on the sheath relative to the knife, so that the mouth of the tube 33 bears against blade edge 16d. When the sheath is manufactured from plastic, the blade of the knife may actually cut into the end of the sheath. This will actually assist in the handling of the sheath and the knife as a single unit, simplifying the performance of the cutting procedure.

In the alternative embodiment of FIGS. 5 and 6, laparoscopic knife 10' is provided with a modification to its shaft 13' in order to facilitate the combined handling of knife 10' with a conventional laparoscopic sheath 30. In the alternative embodiment of FIGS. 5 and 6, laparoscopic knife 10' has a configuration which is substantially identical to that of knife 10 of FIGS. 1–4a. However, shaft 13' of knife 10' is externally threaded. A locking ring 50 which has a threaded aperture 51 is threadably mounted onto shaft 13, prior to the affixation of handle 19' and blade 16' during the manufacturing process. Preferably, locking ring 50 has a lower configuration and a diameter such that it can positively engage the upper end of laparoscopic sheath 30. Once laparoscopic knife 10' has been inserted into sheath 30 and blade 16' has been brought to bear against bottom edge 34 of tube 33, then locking ring 50 is rotated so that it will move along threads 14 on shaft 13' until locking ring 50 engages downwardly and presses against valve section 36 of sheath 30. In this manner, sheath 30 becomes lockingly engaged between blade edge 16d' and locking ring 50, thus combining laparoscopic knife 10' and sheath 30 into an integral unit which may be grasped by the upper portion of sheath 30 as well as by handle 19' as desired for performing the incision making procedure without having to expend the additional energy and concentration required to press sheath 30 downward against blade 16, as described relative to the embodiments of FIGS. 1–4a.

In a still further alternative embodiment, in which engagement of knife edge 16d against bottom edge 33 is sought to be avoided, locking ring 50 may be provided with threads which may be provided to bite into the typically plastic upper end of the aperture for sheath 30. This will permit the laparoscopic knife to be axially fixed relative to sheath 30 without having to grip the sheath between locking ring 50 and the blade of the laparoscopic knife.

As previously mentioned, in some embodiments of the invention, blade edge 16d in the process of the appropriate positioning of the laparoscopic knife relative to the laparoscopic surgical sheath, may be brought to bear against the lower edge of the laparoscopic sheath. The blade being manufactured according to the method and using the materials as previously described, typically may be brought into contact with a plastic or elastomeric laparoscopic sheath without being dulled though many surgical operations. Indeed, the blade edge may bite into the lower edge of the tube of the laparoscopic sheath during the process of positioning and performing the incision procedure. This may, in effect, provide a stabilizing location of the blade of the knife relative to the sheath during the procedure. However, some laparoscopic sheaths are now being fabricated from disposable metal materials. Such metal materials do have the potential for dulling the edge of the blade of the laparoscopic knife of the present invention, thus requiring either resharpening of the blade (which may be impractical and/or cost prohibitive) or the more frequent replacement of the laparoscopic knife as a unit than would otherwise be required. Accordingly, FIG. 7 illustrates a modified blade 16' which is configured for reducing the wear on the blade edge 16d" which might result from encounters with metallic laparoscopic sheath tubes.

In the alternative embodiment of FIG. 7, blade 16" is provided with a notch 16e between shaft 16d" and blade portion 16a". Notch 16e may have a depth of approximately 2–3 mm and a width which is slightly greater than the wall thickness of the laparoscopic sheath tubes which may be encountered. Upon positioning of the laparoscopic knife in the tube of the laparoscopic sheath, the lowermost edge of the tube of the sheath will slip into and be captured by notch 16e. Preferably, the fit will be a snug, but not binding, fit.

This will laterally locate the end of the laparoscopic sheath tube relative to the laparoscopic knife and help hold the knife in place relative to the tube during the incision procedure, thus tending to preclude undesired separation or movement of the knife relative to the sheath tube and preventing undesired bumping of the knife edge 16d''' against the end of the sheath tube. If a notch is not provided in the blade of the laparoscopic knife, then, in order to prevent such bumping, the sheath should be pulled upward away from the blade, in order to clear the blade during the incision procedure.

The blade portion and corresponding blade edge of the blades of the embodiments of FIGS. 1–4a, 5 and 6, and 7, are all shown in an orientation in which both the blade portion 16 (16a', 16a'') is generally perpendicular to the shaft portion 16b (16b', 16b'') of the blade, so that each of the blade edges are arranged at a right angle to the blade shaft and, in turn, the main shaft of the laparoscopic knife of the respective embodiment.

In order to provide a longer edge and an improved cutting action, the blades 16''', 16'''', 16''''' are shown in FIG. 8. In the configurations, 16''' and 16'''', the blade edge will make an angle with the blade shaft of approximately 120–140°, preferably 130°. These blade configurations may be used in combination with any or all of the features of the several previously discussed embodiments. By making the blade edge have a non-perpendicular orientation relative to the shaft, a true slicing action is provided, in which the blade is moving in a non-perpendicular direction relative to the tissue being cut, which is a more efficient cutting action. The blade configurations of FIGS. 1–7 are all such that a direct pulling of the blade edges perpendicularly into the tissue to be cut is required. The blade configurations of FIG. 8 enable the blade edges to slide and slice relative to the tissue providing a more efficient cut with less direct pulling force being required.

Figure 11:
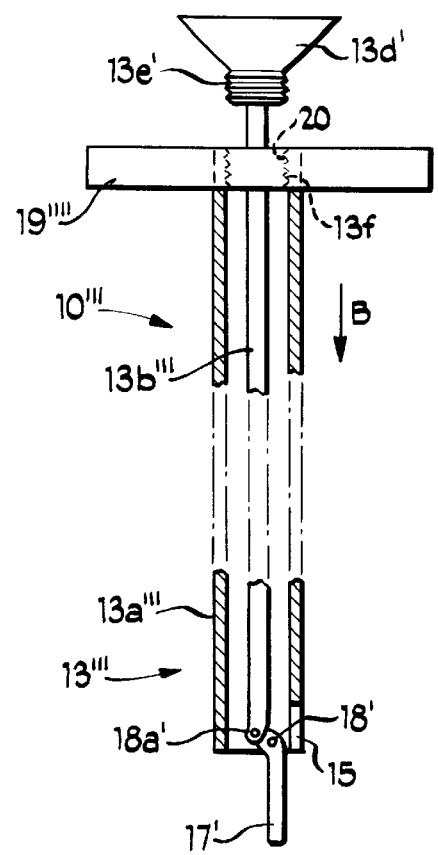
FIG. 11 is a side elevation, partially in section, of a still further alternative embodiment of the articulable laparoscopic knife, having a different locking mechanism than that depicted in FIG. 10.

FIGS. 9–11 illustrate two still further alternative embodiments of the laparoscopic knife of the present invention. In the embodiments of FIGS. 9–11, a laparoscopic knife is provided which has a diameter at its blade end which is defined by the diameter of the shaft 13'''. In the embodiments of FIGS. 9, 10 and 11, shaft 13''' of laparoscopic knife 10 is substantially hollow and provided with a longitudinally running slot 15 on one side of the end of the tube. Blade 17 will be pivotably mounted to tube 13''' so that by either a pushing force on the end 17a or by a pulling force on an alternatively provided end 17b (shown in broken lines), blade 17 will be caused to pivot in a counter-clockwise manner (as shown in FIG. 9), to assume a position extending outwardly through slot 15.

FIG. 10 illustrates an embodiment of the invention corresponding to the version of blade 17 having the lever portion 17b. Blade 17 is pivotably connected to tube 13a''' by pivot pin 18. Blade 17 is connected by pivot pin 18a to shaft 13b''' which is slidably mounted inside tube 13a'''. Shaft 13b''' passes through an aperture (in handle 19''') which may have a configuration similar to the handles in the other embodiments of the laparoscopic knife of the present invention. The distal end of shaft 13b''' is threaded at 13c. A locking disk 13d has a threaded aperture 13e configured to engage the threads at 13c. In order to deploy blade 17, shaft 13b''' is pulled in the direction of arrow A causing blade 17 to pivot about pivot pin 18. Once the desired orientation of blade 17 has been attained, locking disk 13d is spun around threads at 13c until disk 13d abuts and bindingly engages against handle 19'''. In this manner, blade 17 will be locked into its deployed position. Upon completion of the incision, disk 13d may be released, and the blade retracted, to enable removal of the knife separately from the sheath.

An alternative embodiment of the articulable laparoscopic knife is illustrated in FIG. 11, corresponding to the version of the blade 17, shown in solid lines in FIG. 9. In the embodiment of FIG. 11, blade 17' has a slightly different configuration from blade 17 such that a pushing force on shaft 13b'''' causes blade 17' to rotate about pivot pin 18' in a counter-clockwise manner in order to extend through slot 15 to a deployed position. In order to lock laparoscopic knife apparatus 10''' into a deployed configuration, preferably shaft 13b'''' will have a knob 13d' having at one end a plurality of threads 13e'. The threads 13e' will be configured to engage threads 13f provided on the interior of aperture 20 of handle 19''''. Knob 13d' preferably will be configured to be rotatable relative to shaft 13b'''', in a manner readily attainable by one of ordinary skill in the art having the present disclosure before them. Once shaft 13b'''' has been pressed downwardly, as indicated in the direction of arrow B, and blade 17' is swung upwardly and outwardly to its desired deployed configuration, threads 13e' will be brought into engagement with threads 13f and tightened down into handle 19'''' to axially fix shaft 13b'''' relative to tube 13a'''', thus blocking blade 17' in its deployed position.

Figure 12:
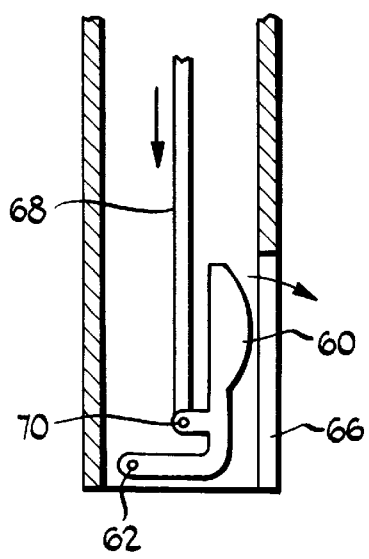
FIG. 12 is a side elevation, partially in section, of another alternative embodiment of the articulable laparoscopic knife, having a cutting end in which the blade pivots downwardly and outwardly.

FIG. 12 is a side elevation, partially in section, of another alternative embodiment of the articulable laparoscopic knife, having a cutting end in which the blade pivots downwardly and outwardly. Blade 60 is mounted on pin 62 to pivot relative to the end of tube 64. Tube 64 has a longitudinally extending slot 66, one face of which is shown in FIG. 12. Shaft 68 (similar to shaft 13b'''' of FIG. 11) is pivotably connected to blade 60 by pin 70. When shaft 68 is pushed downward (toward the blade end of tube 64), blade 60 pivots clockwise downward and outward through slot 66, to the deployed position. A locking mechanism, such as that described with respect to FIG. 11, may be provided at the opposite end of the knife, to hold the blade in the deployed position, until the incision procedure is completed. Thereafter, the locking mechanism (if any) may be released and the shaft 68 pulled upwardly, to retract the blade 60.

Figure 13:
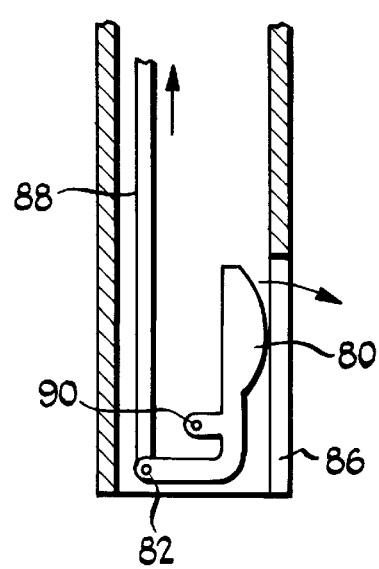
FIG. 13 is a side elevation, partially in section, of another alternative embodiment of the articulable laparoscopic knife, having a cutting end in which the blade pivots downwardly and outwardly.

FIG. 13 is a side elevation, partially in section, of another alternative embodiment of the articulable laparoscopic knife, having a cutting end in which the blade pivots downwardly and outwardly. Blade 80 is mounted on pin 82 to pivot relative to the end of tube 84. Tube 84 has a longitudinally extending slot 86, one face of which is shown in FIG. 13. Shaft 88 (similar to shaft 13b'''' of FIG. 10) is pivotably connected to blade 80 by pin 90. When shaft 88 is pulled upward (away from the blade end of tube 84), blade 80 pivots clockwise downward and outward through slot 86, to the deployed position. A locking mechanism, such as that described with respect to FIG. 10, may be provided at the opposite end of the knife, to hold the blade in the deployed position, until the incision procedure is completed. Thereafter, the locking mechanism (if any) may be released and the shaft 88 pulled upwardly, to retract the blade 80.

The articulable laparoscopic knife configurations of FIGS. 9, 10 and 11, and 12 and 13 permit the construction of a laparoscopic knife having a cutting edge which is substantially greater in potential length than the available diameter of either the shaft 13''' or of the laparoscopic sheath tube with which the laparoscopic knife is intended to be used, thus enabling a greater amount of extension of the peritoneal incision than that possible with the embodiments of FIGS. 1–8. In addition, the laparoscopic knife of the embodiments of FIGS. 9, 10 and 11, and 12 and 13, may also be provided with a further locking ring, such as locking ring 50, for enabling the locking engagement of the laparoscopic knife to the laparoscopic sheath in the manner described with respect to FIGS. 5 and 6. In addition, the actual blade portion of the blades 17, 17' may be substantially straight and elongated as illustrated in FIGS. 9, 10 and 11, or the blades may be of varying configuration, such as the notched blade of FIG. 7, or the varying blade configurations of FIG. 8.

Although the laparoscopic knives of the preferred embodiments of the present invention have been described and discussed with respect to laparoscopic surgical procedures, such as the removal of a gall bladder, it is contemplated that the present invention may have applicability in other surgical procedures wherever a controlled incision within a body cavity or beneath a body wall is desired in which the incision is desired to be made from an inside position to an outer position, without departing from the scope of the present invention.

The foregoing description and drawings merely explain and illustrate the invention. The invention is not limited thereto except to the extent that the appended are so limited, as those skilled in the art who have the disclosure before them would be able to make modifications and variations therein without departing from the scope of the invention.

We claim:

1. A laparoscopic knife apparatus, for use in surgical procedures, for enabling the contiguous enlargement of existing surgical incisions in difficult to access locations, comprising:

a shaft member, having a longitudinal axis and first and second ends;

a blade member, operably affixed to the first end of the shaft member, extending laterally from the shaft member;

the blade member having an elongated cutting edge extending substantially contiguously from the shaft member;

the cutting edge of the blade member extending at a substantially oblique angle relative to the longitudinal axis of the shaft member;

a handle member, operably affixed to the second end of the shaft member, the blade member being oriented relative to the shaft member so that the cutting edge of the blade member points substantially generally back toward the handle member, so that upon placement of the cutting edge against a surface to be cut, a pulling motion on the handler member, and in turn, a pulling motion upon the laparoscopic knife apparatus as a whole, prompts a cutting motion of the blade member relative to the surface to be cut.

2. The laparoscopic knife apparatus according to claim 1, wherein the blade member has a longitudinal axis extending from the shaft member at an angle substantially obliquely relative to the longitudinal axis of the shaft member, wherein the laparoscopic knife apparatus further comprises:

means, operably associated with the handle member, for indicating the direction of the blade member, when the blade member is inserted within a patient.

3. The laparoscopic knife apparatus according to claim 1, further comprising means for facilitating use of the laparoscopic knife apparatus with a laparoscopic sheath, for enabling a laparoscopic sheath to be used to facilitate handling of the laparoscopic knife apparatus.

4. The laparoscopic knife apparatus according to claim 3, wherein the means for facilitating use with a laparoscopic sheath comprises:

a notch, operably disposed in the blade member, at a position proximate a juncture between the shaft member and the blade member, for engaging and receiving an edge of a lower opening of a laparoscopic sheath tube, for facilitating the coordinated combined movement of the laparoscopic knife with a laparoscopic sheath while performing an incision procedure with same.

5. The laparoscopic knife apparatus according to claim 1, further comprising means for affixing the laparoscopic knife apparatus in position with respect to a laparoscopic sheath within which the knife apparatus has been inserted.

6. The laparoscopic knife apparatus according to claim 1, further comprising means for articulating the blade member from a stowed position within the shaft member, to a deployed position at least partially external to the shaft member.

7. The laparoscopic knife apparatus according to claim 1, wherein the cutting edge of the blade member has an arcuate configuration.

8. The laparoscopic knife apparatus according to claim 1, wherein the blade member has a triangular configuration.

9. The laparoscopic knife apparatus according to claim 1, wherein the cutting edge is straight.

10. The laparoscopic knife apparatus according to claim 1, wherein the cutting edge makes an included angle with the shaft member in the range of 120°–140°.

11. The laparoscopic knife apparatus according to claim 1, wherein the blade member has a wedge-shaped cross-sectional configuration, in a direction substantially transverse to the cutting edge.

12. A laparoscopic knife apparatus, for use in surgical procedures, for enabling the contiguous enlargement of existing surgical incisions in difficult to access locations, comprising:

a shaft member, having a longitudinal axis and first and second ends;

a blade member, operably affixed to the first end of the shaft member, the blade member having an elongated cutting edge extending substantially contiguously from the shaft member;

the cutting edge of the blade member extending at a substantially oblique angle relative to the longitudinal axis of the shaft member;

a handle member, operably affixed to the second end of the shaft member, the blade member being oriented relative to the shaft member so that the cutting edge of the blade member points substantially generally toward the handle member, so that upon placement of the cutting edge against a surface to be cut, a pulling motion on the handle member, and in turn, a pulling motion upon the laparoscopic knife apparatus as a whole, prompts a cutting motion of the blade member relative to the surface to be cut;

the blade member having a longitudinal axis extending from the shaft member at an angle substantially obliquely relative to the longitudinal axis of the shaft member;

means, operably associated with the handle member, for indicating the direction of the blade member, when the blade member is inserted within a patient;

the means, operably associated with the handle member, for indicating the direction of the blade member, when the blade member is inserted within a patient, further comprising the handle member having an arrowhead configuration, wherein a pointed portion of the arrowhead configuration points in the same direction as the blade member.

13. A laparoscopic knife apparatus, for use in surgical procedures, for enabling the contiguous enlargement of existing surgical incisions in difficult to access locations, comprising:

a shaft member, having a longitudinal axis and first and second ends;

a blade member, operably affixed to the first end of the shaft member, the blade member having an elongated cutting edge extending substantially contiguously from the shaft member;

the cutting edge of the blade member extending at a substantially oblige angle relative to the longitudinal axis of the shaft member;

a handle member, operably affixed to the second end of the shaft member, the blade member being oriented relative to the shaft member so that the cutting edge of the blade member points substantially generally toward the handle member, so that upon placement of the cutting edge against a surface to be cut, a pulling motion on the handle member, and in turn, a pulling motion upon the laparoscopic knife apparatus as a whole, prompts a cutting motion of the blade member relative to the surface to be cut;

means for affixing the laparoscopic knife apparatus in position with respect to a laparoscopic sheath within which the knife apparatus has been inserted;

the means for affixing the laparoscopic knife apparatus in position with respect to a laparoscopic sheath within which the knife apparatus has been inserted further comprising:

a locking ring, having a diameter greater than a top portion of the laparoscopic sheath, the locking ring circumferentially surrounding at least a portion of the shaft member and threadably engaged therewith, so that upon screwing down of the locking ring on the shaft member toward the top portion of a laparoscopic sheath through which the shaft member of the knife apparatus is inserted, and upon engagement of an edge of a lower opening of the laparoscopic sheath with the blade member, the laparoscopic sheath becomes clamped between the blade member and the locking ring, to form an integrated unit for facilitated handling thereof.

14. A laparoscopic knife apparatus, for use in surgical procedures, for enabling the contiguous enlargement of existing surgical incisions in difficult to access locations, comprising:

a shaft member, having a longitudinal axis and first and second ends;

a blade member, operably affixed to the first end of the shaft member, the blade member having an elongated cutting edge extending substantially continuously from the shaft member;

the cutting edge of the blade member extending at a substantially oblique angle relative to the longitudinal axis of the shaft member;

a handle member, operably affixed to the second end of the shaft member, the blade member being oriented relative to the shaft member so that the cutting edge of the blade member points substantially generally toward the handle member, so that upon placement of the cutting edge against a surface to be cut, a pulling motion on the handle member, and in turn, a pulling motion union the laparoscopic knife apparatus as a whole, prompts a cutting motion of the blade member relative to the surface to be cut;

means for articulation the blade member from a slowed position within the shaft member, to a deployed position at least partially external to the shaft member;

the means for articulating the blade member from a stowed position within the shaft member, to a deployed position at least partially external to the shaft member further comprising:

the shaft member being configured as a tubular member, having a longitudinally extending slot disposed in a lower end region thereof;

the blade member having a proximal end thereof pivotably mounted within the tubular member proximate the longitudinally extending slot, so that upon pivoting of the blade member, a distal end of the blade member can be moved between the stowed position within the shaft member and the deployed position at least partially external to the shaft member;

a plunger member, positioned within the tubular member and extending from a lower end proximate the lower end region of the tubular member, up the tubular member and through an aperture in the handle member, the plunger member being pivotably connected at its lower end, to the blade member;

whereupon vertical movement of the plunger member causes the blade member to be pivoted between the stowed position within the shaft member and the deployed position at least partially external to the shaft member.

* * * * *

UNITED STATES PATENT AND TRADEMARK OFFICE
CERTIFICATE OF CORRECTION

PATENT NO : 6,051,005
DATED : April 18, 2000
INVENTOR(S) : Brandsey et al.

It is certified that error appears in the above-identified patent and that said Letters Patent are hereby corrected as shown below:

| | |
|---|---|
| Column 9, Line 48 | Delete "handler" and insert instead --handle-- |
| Column 12, Line 7 | Delete "continuously" and insert instead -- contiguously-- |
| Column 12, Line 19 | Delete "union" and insert instead --upon-- |
| Column 12, Line 24 | Delete "articulation" and insert instead --articulating-- |
| Column 12, Line 24 | Delete "slowed" and insert instead --stowed-- |

Signed and Sealed this

Seventeenth Day of April, 2001

Attest:

NICHOLAS P. GODICI

Attesting Officer

Acting Director of the United States Patent and Trademark Office